US010295638B2

(12) United States Patent
Sugiura

(10) Patent No.: US 10,295,638 B2
(45) Date of Patent: May 21, 2019

(54) IMAGE PROCESSING APPARATUS, IMAGE DIAGNOSTIC APPARATUS AND IMAGE PROCESSING METHOD

(75) Inventor: Satoshi Sugiura, Otawara (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 1903 days.

(21) Appl. No.: 12/145,089

(22) Filed: Jun. 24, 2008

(65) Prior Publication Data

US 2009/0005672 A1    Jan. 1, 2009

(30) Foreign Application Priority Data

Jun. 28, 2007 (JP) .................................. 2007-169989
May 9, 2008 (JP) .................................. 2008-123129

(51) Int. Cl.
| | | |
|---|---|---|
| *A61B 5/055* | (2006.01) | |
| *G01R 33/563* | (2006.01) | |
| *G06T 17/00* | (2006.01) | |
| *G01R 33/56* | (2006.01) | |
| *G16H 40/63* | (2018.01) | |

(52) U.S. Cl.
CPC ........ *G01R 33/56366* (2013.01); *G06T 17/00* (2013.01); *G01R 33/5601* (2013.01); *G16H 40/63* (2018.01)

(58) Field of Classification Search
None
See application file for complete search history.

(56) References Cited

U.S. PATENT DOCUMENTS

| | | | | |
|---|---|---|---|---|
| 5,800,355 A | * | 9/1998 | Hasegawa | ...................... 600/436 |
| 6,147,759 A | * | 11/2000 | Simmons et al. | ............ 356/623 |
| 2004/0139049 A1 | * | 7/2004 | Hancock et al. | ................. 707/1 |
| 2005/0059876 A1 | * | 3/2005 | Krishnan et al. | ............. 600/407 |
| 2006/0241402 A1 | * | 10/2006 | Ichihara et al. | ............... 600/425 |
| 2007/0014452 A1 | * | 1/2007 | Suresh et al. | ................. 382/128 |
| 2007/0203412 A1 | | 8/2007 | Sugiura | |
| 2007/0258631 A1 | | 11/2007 | Friedman et al. | |

FOREIGN PATENT DOCUMENTS

| | | |
|---|---|---|
| JP | 2005-137558 | 6/2005 |
| JP | 2006-087626 | 4/2006 |

OTHER PUBLICATIONS

Sakuma et al., "Diagnosis of Ischemic Heart Disease by Means of Contrast Enhanced MRI", INNERVISION, vol. 15, No. 13, pp. 59-66, (2000).
Takase et al., "Assessment of Myocardial Perfusion and Viability Using MRImaging", NICHIJIISHI (JJMR), vol. 23, No. 4, pp. 166-180, (2003).
JP Office Action dated Feb. 5, 2013 in JP 2008-123129.

* cited by examiner

*Primary Examiner* — Jennifer Deiterle
(74) *Attorney, Agent, or Firm* — Nixon & Vanderhye P.C.

(57) ABSTRACT

An image processing apparatus includes an image data acquisition unit, a development generating unit and a display unit. The image data acquisition unit acquires slice image data with regard to a heart of an object. The development generating unit obtains blood flow perfusion information with regard to a myocardial thickness direction based on the slice image data and generates development data according to a desired development format for displaying the blood flow perfusion information. The display unit displays the development data.

23 Claims, 11 Drawing Sheets

IMAGE PROCESSING APPARATUS, IMAGE DIAGNOSTIC APPARATUS AND IMAGE PROCESSING METHOD

This application claims priority to Japan Application No. 2007-169989, filed Jun. 28, 2007, and Japan Application No. 2008-123129, filed 9 May 2008, the entire contents of each of which are hereby incorporated by reference.

BACKGROUND

1. Technical Field

The present invention relates to an image processing apparatus and method display a myocardial perfusion image.

2. Description of Related Art

Magnetic Resonance Imaging (MRI) is an imaging method which excites nuclear spins of an object set in a static magnetic field with a radio frequency (RF) signal having the Larmor frequency magnetically and reconstructs an image based on a nuclear magnetic resonance (NMR) signal generated due to the excitation.

In the diagnosis of ischemic heart disease, as a method for evaluating myocardial blood flow perfusion by means of MRI, a method is known in which multi-slice dynamic longitudinal relaxation (T1) weighted imaging is performed for obtaining a left ventricular short axis image during the first circulation in synchronized with an ECG (electrocardiogram) after a contrast medium is injected into a vein and enhancing process of the myocardium is observed (myocardial perfusion) (see, for example, Japanese Patent Application (Laid-Open) No. 2006-87626). With regard to the images thus acquired, each of the left ventricular short axis tomographic images is divided into multiple radial regions. Then, the images thus divided are converted into development images in which the regions thus divided are concentrically arranged from the cardiac base part toward the apex cordis part, following which the development images thus converted are displayed.

FIG. 1 is a diagram showing MR images of respective sections acquired at respective dynamic time phases by a conventional myocardial perfusion imaging.

FIG. 1 shows an example of MR images 1-1, 2-1, 3-1, 1-2, 2-2, 3-2, . . . , 1-30, 2-30, and 3-30, acquired by myocardial perfusion imaging. In this example, the number of slices is a total of three sections consisting of slices 1, 2, and 3 from the apex cordis part toward the cardiac base part, and the number of dynamic time phases is 30.

Then, the myocardiums on the MR images are divided into multiple sub-regions radially, and a dynamic curve is created based upon the average image value in each sub-region. The dynamic curve is a graph representing the image value changing over time. For example, a dynamic curve A is created for the sub-region A. Further, a dynamic curve B is created for the sub-region B.

FIG. 2 shows conventional developments indicating myocardial blood flow information generated based on dynamic curves in respective small regions shown in FIG. 1. The innermost ring represents a lower cross-section of an entire ventricular wall width (divided circumferentially into eight sections). The middle ring represents an intermediate cross-section of an entire ventricular wall width (divided circumferentially into eight sections). The outermost ring represents an upper cross-section of an entire ventricular wall width (divided circumferentially into 8 sections).

As shown in FIG. 2, a dynamic curve is created for each small region with the vertical axis representing the image signal value, and the horizontal axis representing time. Specifically, FIG. 2 shows the dynamic curves A and B that correspond to the small regions A and B shown in FIG. 1, respectively. Furthermore, various parameters are calculated based upon the dynamic curves A, B, . . . and development images are created with colors or a gray scale associated with the parameter values thus calculated. For example, in FIG. 2, the maximum values of the image signals and the times till the maximum gradients of the dynamic curves are calculated as the parameters, and the parameters thus calculated are displayed in the development image 1 and the development image 2, respectively. Such a development image is called a bull's-eye. In the bull's-eye, the inner side of the concentric circular image corresponds to the apex cordis part, and the outer side thereof corresponds to the cardiac base part.

FIG. 3 is a diagram indicating correspondence relationship between myocardial left ventricular short axis MR images and the conventional development representing myocardial blood flow information as shown in FIG. 2.

FIG. 3 shows the relations between MR tomographic images of the myocardium in the left ventricular short axis direction and the small regions in the development image. For example, each small region positioned on the inner side of the development image corresponds to a region divided at the apex cordis part of the myocardium. Each small region positioned in the intermediate part of the development image corresponds to a region divided at the intermediate part of the myocardium. Each small region positioned on the outer side of the development image corresponds to a region divided at the cardiac base part of the myocardium.

FIG. 4 is a diagram showing symptom of subendocardial ischemia schematically by slicing a heart into rings.

In the heart which has developed subendocardial ischemia, blood is not supplied to the inner side of the myocardium, and the medical condition progresses from the inner side toward the outer side of the myocardium. However, the conventional bull's-eye is created by dividing each slice image only radially, and not in the thickness direction of the myocardium. Accordingly, the conventional bull's-eye does not provide precise information with respect to blood flow perfusion that represents the range of ischemia along the myocardial thickness direction.

In particular, magnetic resonance imaging apparatuses generally allow data to be acquired with a high spatial resolution as compared with a method such as a nuclear medicine examination, thereby providing an advantage of depicting a subendocardial ischemia, which has been reported. However, the conventional development image display lacks information with respect to the myocardium along the thickness direction, leading to a problem in that the subendocardial ischemia cannot be evaluated. This is common problem not only for magnetic resonance imaging apparatuses but for any other diagnostic medical imaging apparatuses which are capable of acquiring image data with high spatial resolutions.

BRIEF SUMMARY

The present exemplary embodiment has been made in light of the conventional situations, and it is an object of the present invention to provide an image processing apparatus, an image diagnostic apparatus and an image processing method which can display information concerning a myocardial blood flow perfusion in a myocardial thickness direction.

The present exemplary embodiment provides an image processing apparatus comprising: an image data acquisition unit configured to acquire slice image data with regard to a heart of an object; a development generating unit configured to obtain blood flow perfusion information with regard to a myocardial thickness direction based on the slice image data and generate development data according to a desired development format for displaying the blood flow perfusion information; and a display unit configured to display the development data, in an aspect to achieve the object.

The present exemplary embodiment also provides an image processing apparatus comprising: an image data acquisition unit configured to acquire slice image data with regard to a heart of an object; a development generating unit configured to calculate desired information based on a pixel value in a divided region generated by dividing the slice image data at least in a myocardial thickness direction and generate development data according to a desired development format for displaying the desired information; and a display unit configured to display the development data, in an aspect to achieve the object.

The present exemplary embodiment also provides an image diagnostic apparatus comprising: an image acquisition unit configured to acquire slice image data with regard to a heart of an object by imaging of the heart; a development generating unit configured to obtain blood flow perfusion information with regard to a myocardial thickness direction based on the slice image data and generate development data according to a desired development format for displaying the blood flow perfusion information; and a display unit configured to display the development data, in an aspect to achieve the object.

The present exemplary embodiment also provides an image processing method comprising: acquiring slice image data with regard to a heart of an object; obtaining blood flow perfusion information with regard to a myocardial thickness direction based on the slice image data and generating development data according to a desired development format for displaying the blood flow perfusion information; and displaying the development data, in an aspect to achieve the object.

The present exemplary embodiment also provides an image processing method comprising: acquiring slice image data with regard to a heart of an object; calculating desired information based on a pixel value in a divided region generated by dividing the slice image data at least in a myocardial thickness direction and generating development data according to a desired development format for displaying the desired information; and displaying the development data, in an aspect to achieve the object.

The present exemplary embodiment as described above makes it possible to display information concerning a myocardial blood flow perfusion in a myocardial thickness direction.

DESCRIPTION OF THE PREFERRED EMBODIMENTS

An image processing apparatus, an image diagnostic apparatus and an image processing method according to an embodiment of the present invention will be described with reference to the accompanying drawings.

Figure 1:
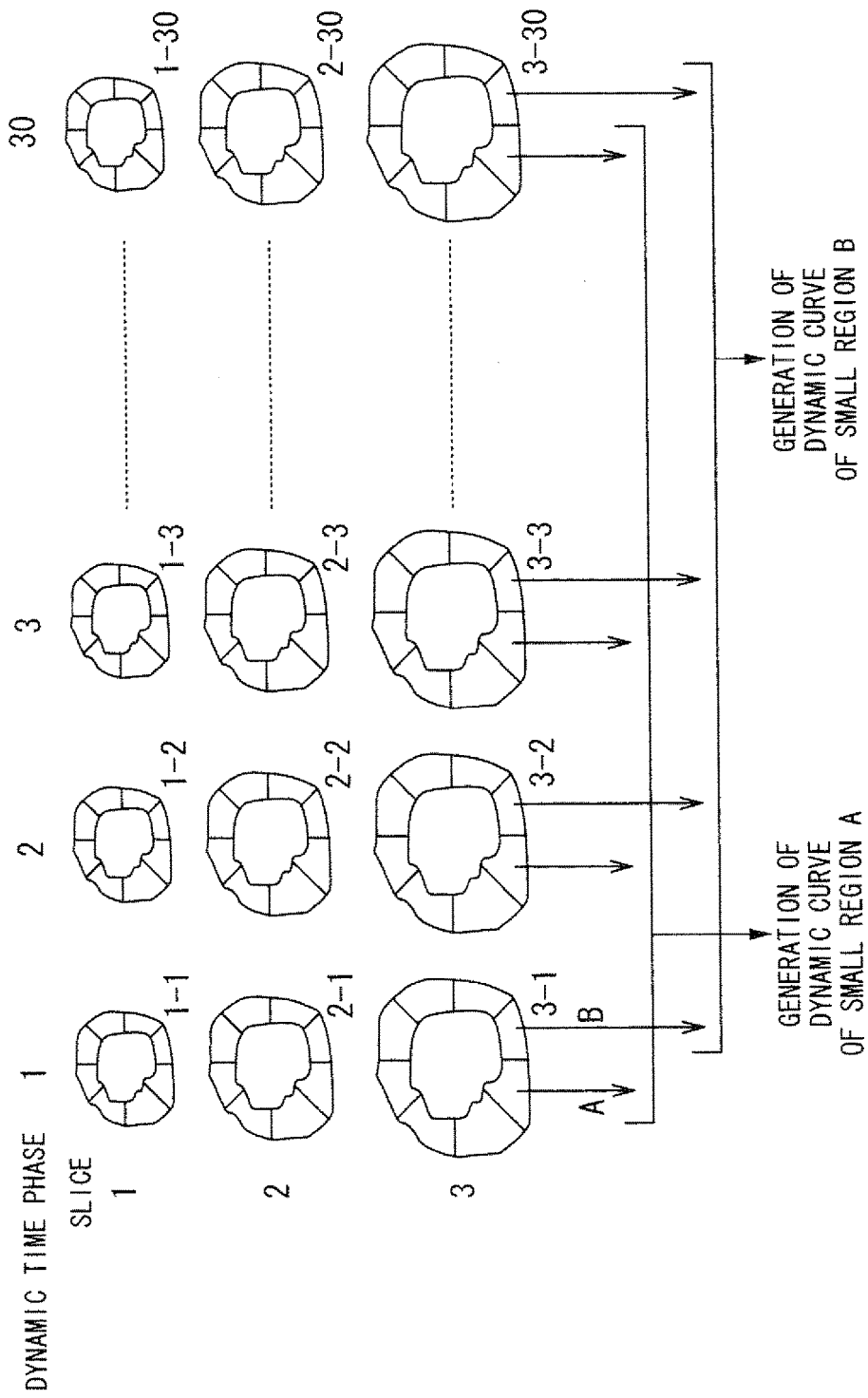
FIG. 1 is a diagram showing MR images of respective sections acquired at respective dynamic time phases by a conventional myocardial perfusion imaging.
Figure 2:
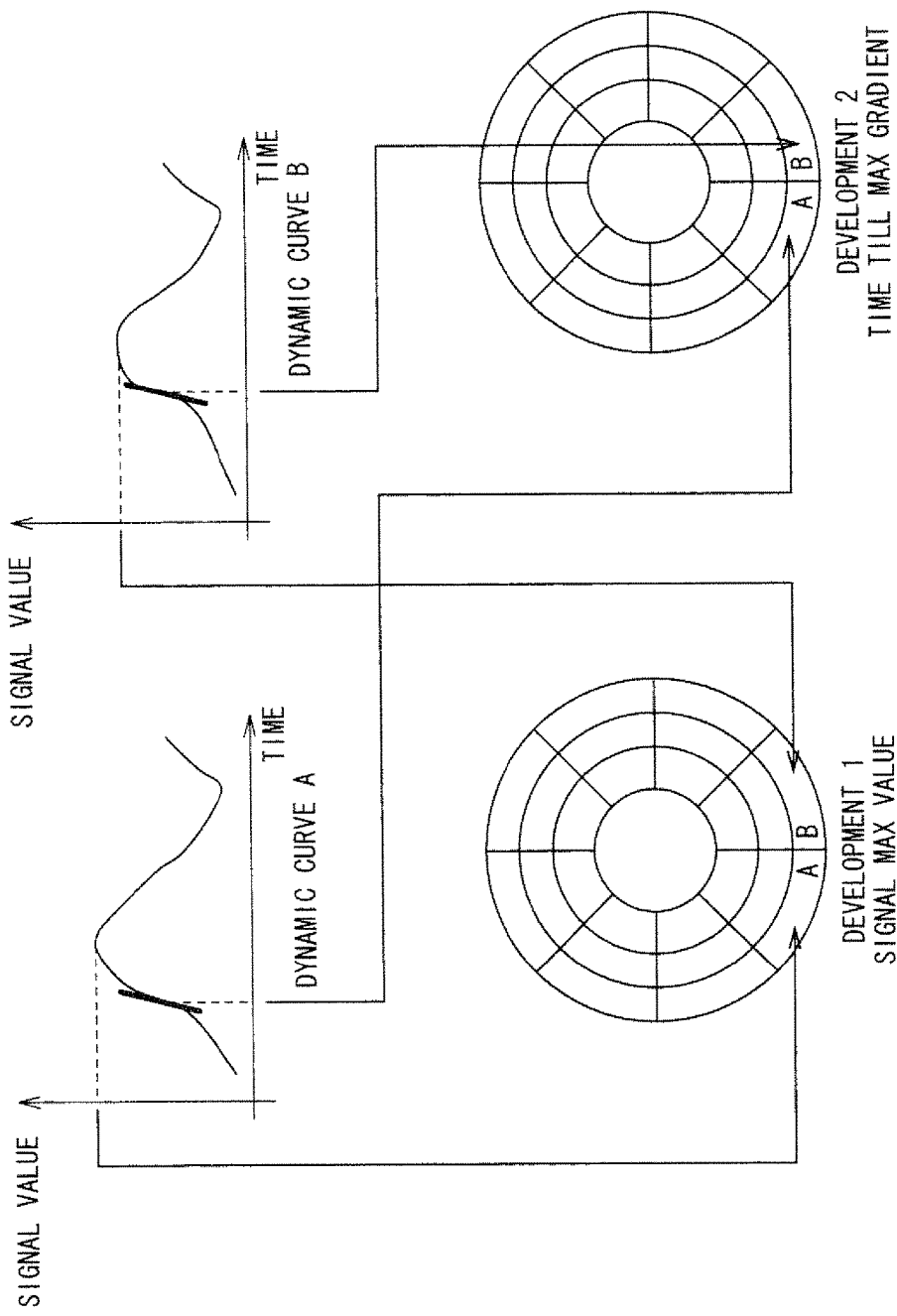
FIG. 2 shows conventional developments indicating myocardial blood flow information generated based on dynamic curves in respective small regions shown in FIG. 1.
Figure 3:
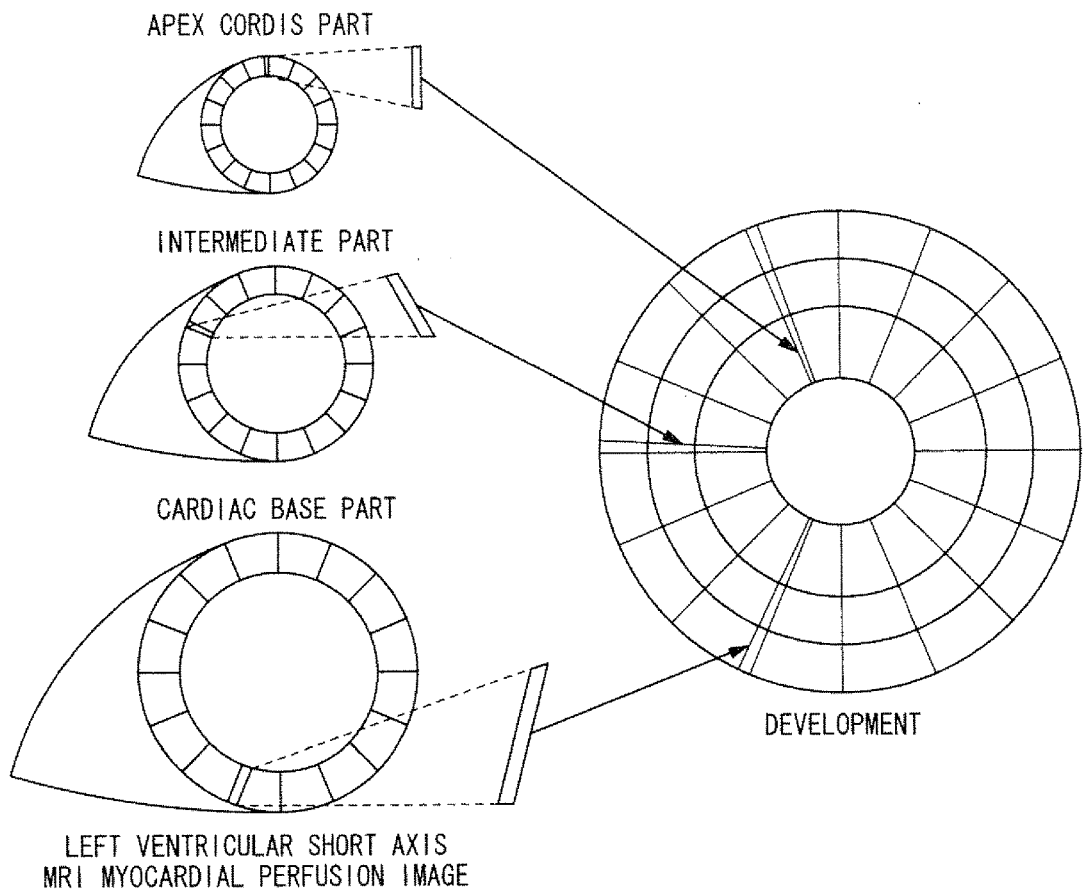
FIG. 3 is a diagram indicating correspondence relationship between myocardial left ventricular short axis MR images and the conventional development representing myocardial blood flow information as shown in FIG. 2.
Figure 4:
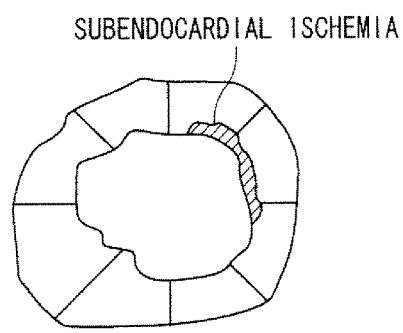
FIG. 4 is a diagram showing symptom of subendocardial ischemia schematically by slicing a heart into rings.
Figure 5:
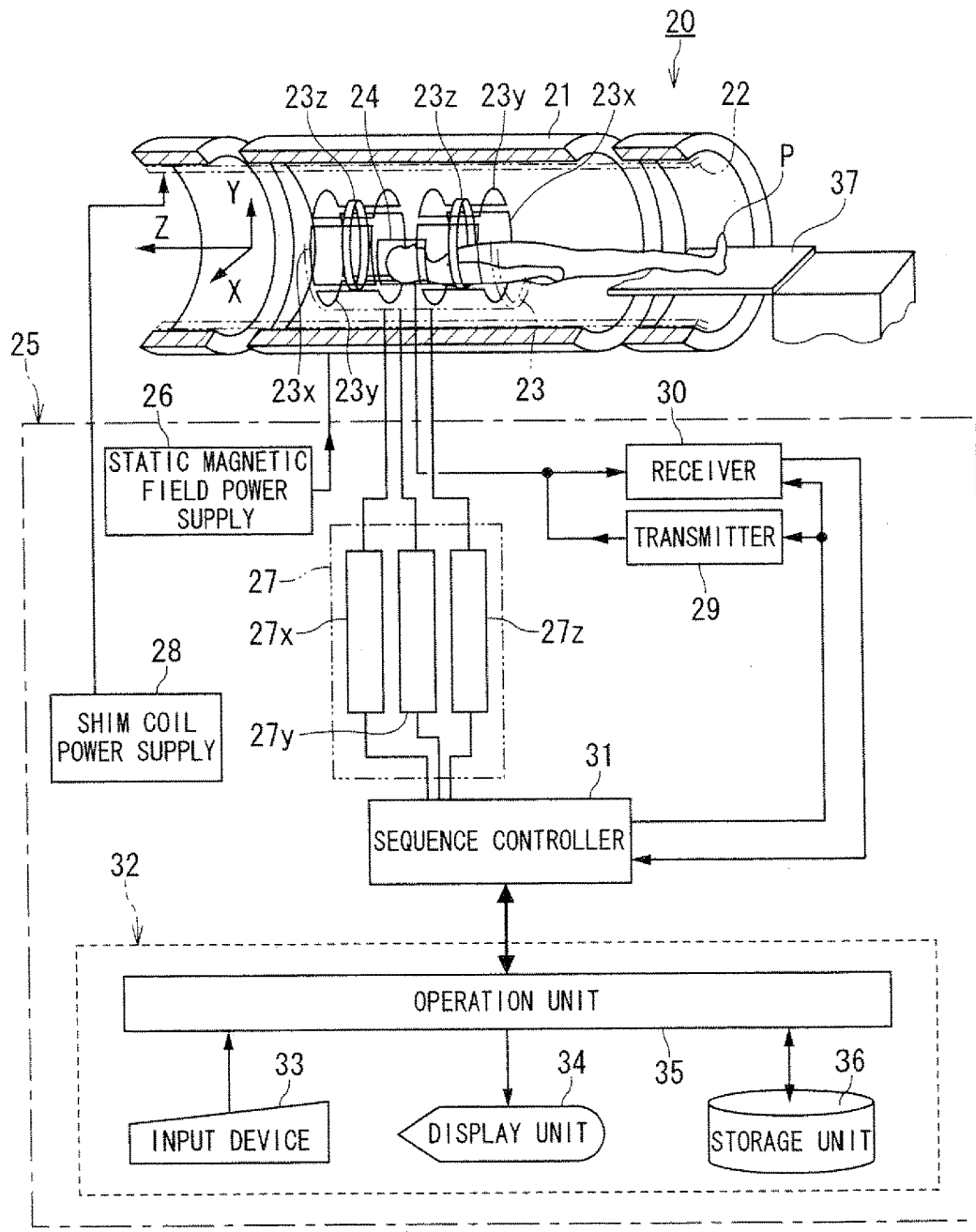
FIG. 5 is a block diagram showing an embodiment of magnetic resonance imaging apparatus as an example of image diagnostic apparatus having an image processing apparatus according to an exemplary embodiment of the present invention.

FIG. 5 is a block diagram showing an embodiment of magnetic resonance imaging apparatus as an example of image diagnostic apparatus having an image processing apparatus according to of the present invention.

A magnetic resonance imaging apparatus 20 includes a static field magnet 21 for generating a static magnetic field, a shim coil 22 arranged inside the static field magnet 21 which is cylinder-shaped, a gradient coil 23 and a RF coil 24. The static field magnet 21, the shim coil 22, the gradient coil 23 and the RF coil 24 are built in a gantry (not shown).

The magnetic resonance imaging apparatus 20 also includes a control system 25. The control system 25 includes a static magnetic field power supply 26, a gradient power supply 27, a shim coil power supply 28, a transmitter 29, a receiver 30, a sequence controller 31 and a computer 32. The gradient power supply 27 of the control system 25 includes an X-axis gradient power supply 27$x$, a Y-axis gradient power supply 27$y$ and a Z-axis gradient power supply 27$z$. The computer 32 includes an input device 33, a display unit 34, an operation unit 35 and a storage unit 36.

The static field magnet 21 communicates with the static magnetic field power supply 26. The static magnetic field power supply 26 supplies electric current to the static field magnet 21 to get the function to generate a static magnetic field in an imaging region. The static field magnet 21 includes a superconductivity coil in many cases. The static field magnet 21 gets current from the static magnetic field power supply 26 which communicates with the static field magnet 21 at excitation. However, once excitation has been made, the static field magnet 21 is usually isolated from the static magnetic field power supply 26. The static field magnet 21 may include a permanent magnet which makes the static magnetic field power supply 26 unnecessary.

The static field magnet 21 has the cylinder-shaped shim coil 22 coaxially inside itself. The shim coil 22 communicates with the shim coil power supply 28. The shim coil power supply 28 supplies current to the shim coil 22 so that the static magnetic field becomes uniform.

The gradient coil 23 includes an X-axis gradient coil 23x, a Y-axis gradient coil 23y and a Z-axis gradient coil 23z. Each of the X-axis gradient coil 23x, the Y-axis gradient coil 23y and the Z-axis gradient coil 23z which is cylinder-shaped is arranged inside the static field magnet 21. The gradient coil 23 has also a bed 37 in the area formed inside it which is an imaging area. The bed 37 supports an object P. Around the bed 37 or the object P, the RF coil 24 may be arranged instead of being built in the gantry.

The gradient coil 23 communicates with the gradient power supply 27. The X-axis gradient coil 23x, the Y-axis gradient coil 23y and the Z-axis gradient coil 23z of the gradient coil 23 communicate with the X-axis gradient power supply 27x, the Y-axis gradient power supply 27y and the Z-axis gradient power supply 27z of the gradient power supply 27 respectively.

The X-axis gradient power supply 27x, the Y-axis gradient power supply 27y and the Z-axis gradient power supply 27z supply currents to the X-axis gradient coil 23x, the Y-axis gradient coil 23y and the Z-axis gradient coil 23z respectively so as to generate gradient magnetic fields Gx, Gy and Gz in the X, Y and Z directions in the imaging area.

The RF coil 24 communicates with the transmitter 29 and the receiver 30. The RF coil 24 has a function to transmit a RF signal given from the transmitter 29 to the object P and receive a NMR signal generated due to an nuclear spin inside the object P which is excited by the RF signal to give to the receiver 30.

The sequence controller 31 of the control system 25 communicates with the gradient power supply 27, the transmitter 29 and the receiver 30. The sequence controller 31 has a function to storage sequence information describing control information needed in order to make the gradient power supply 27, the transmitter 29 and the receiver 30 drive and generate gradient magnetic fields Gx, Gy and Gz in the X, Y and Z directions and a RF signal by driving the gradient power supply 27, the transmitter 29 and the receiver 30 according to a predetermined sequence stored. The control information above-described includes motion control information, such as intensity, impression period and impression timing of the pulse electric current which should be impressed to the gradient power supply 27

The sequence controller 31 is also configured to give raw data to the computer 32. The raw data is complex data obtained through the detection of a NMR signal and A/D (analog to digital) conversion to the NMR signal detected in the receiver 30.

The transmitter 29 has a function to give a RF signal to the RF coil 24 in accordance with control information provided from the sequence controller 31. The receiver 30 has a function to generate raw data which is digitized complex number data by detecting a NMR signal given from the RF coil 24 and performing predetermined signal processing and A/D converting to the NMR signal detected. The receiver 30 also has a function to give the generated raw data to the sequence controller 31.

The computer 32 gets various functions by the operation unit 35 executing some programs stored in the storage unit 36 of the computer 32. However, the magnetic resonance imaging apparatus 20 may include some specific circuits having various functions instead of using some of the programs.

Figure 6:
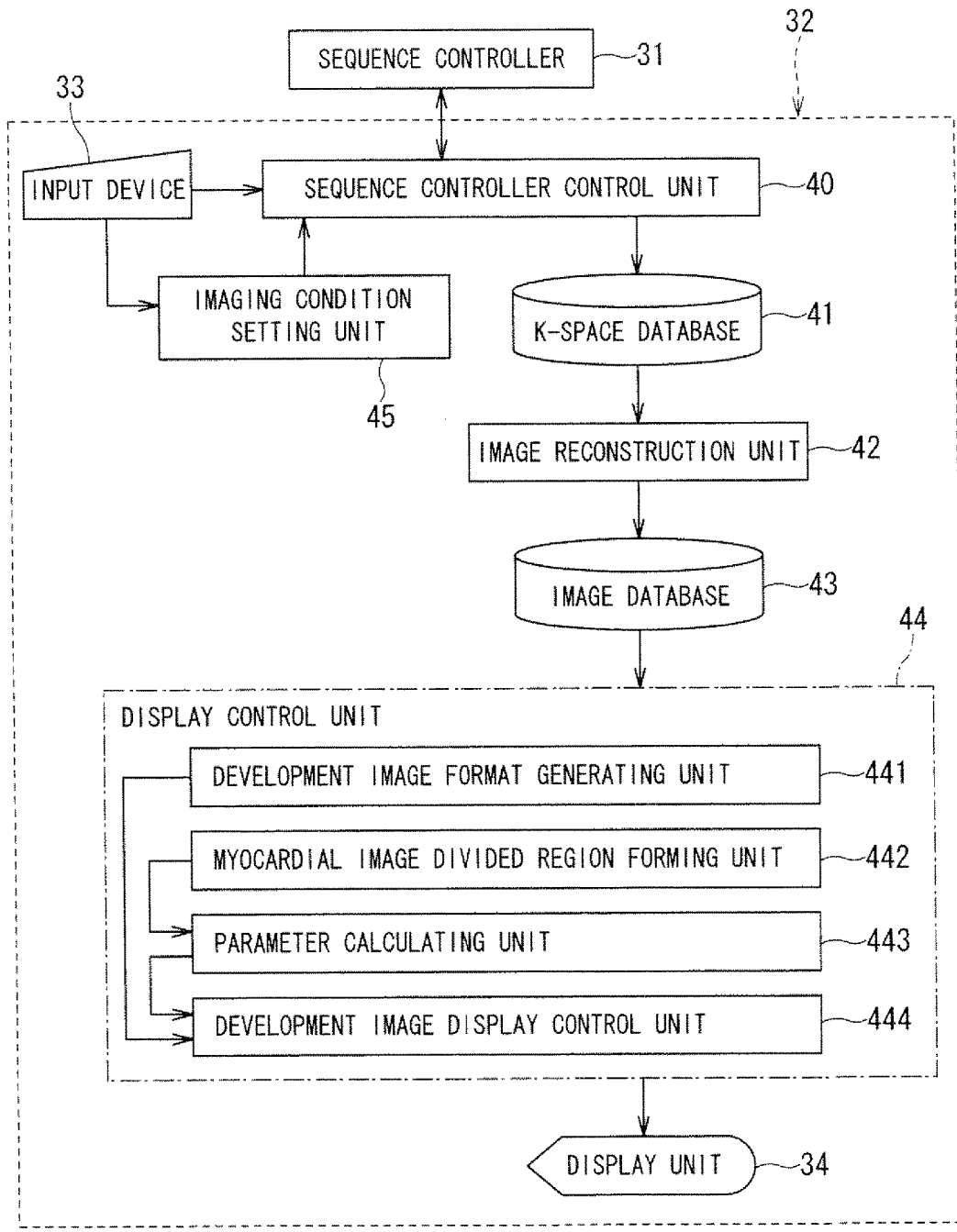
FIG. 6 is a functional block diagram of the computer in the magnetic resonance imaging apparatus shown in FIG. 5.

FIG. 6 is a functional block diagram of the computer 32 in the magnetic resonance imaging apparatus 20 shown in FIG. 5.

The computer 32 functions as a sequence controller control unit 40, a k-space database 41, an image reconstruction unit 42, an image database 43, a display control unit 44 and an imaging condition setting unit 45 by program. Note that, the display control unit 44 works as an image processing apparatus built in the computer 32 of the magnetic resonance imaging apparatus 20 in an example case shown in FIG. 6.

The imaging condition setting unit 45 has a function to set imaging conditions including a pulse sequence based on instruction information from the input device 33 and to provide the set imaging conditions to the sequence controller control unit 40. For this purpose, the imaging condition setting unit 45 has a function to display screen information for setting imaging conditions on the display unit 34.

The sequence controller control unit 40 has a function for controlling the driving of the sequence controller 31 by giving imaging conditions including sequence information set in the imaging condition setting unit 45, to the sequence controller 31 based on information instructing imaging start from the input device 33 or another element. In addition, the sequence controller control unit 40 has a function for receiving raw data from the sequence controller 31 and arranging the raw data to k space (Fourier space) formed in the k-space database 41. Therefore, the raw data generated by the receiver 30 are stored in the k-space database 41 as k space data. That is, the k space data is arranged in the k space formed in the k-space database 41.

The image reconstruction unit 42 has a function for reconstructing image data of the object P by capturing the k-space data from the k-space database 41 and performing image reconstruction processing such as Fourier transform processing to the k-space data, and writing the reconstructed image data to the image database 43. Therefore, image data of the object P is stored in the image database 43.

The display control unit 44 has: a function as an image processing apparatus which generates development image data of a myocardial perfusion image based upon myocardial slice image data acquired by the magnetic resonance imaging apparatus 20, which allows information regarding myocardial blood flow perfusion to be displayed not only along the circumferential direction of the tomographic images of the myocardium but also along thickness directions thereof; and a function of transmitting the development image data thus generated to the display unit 34, thereby displaying a development image of the myocardium on the display unit 34. To achieve this, the display control unit 44 includes a development image format generating unit 441, a myocardial image divided region forming unit 442, a parameter calculating unit 443, and a development image display control unit 444.

The development image format generating unit 441 has a function of generating a desired format of a development image which enables information regarding myocardial blood flow perfusion to be displayed at least in a myocardial thickness direction. The development image format generating unit 441 is capable of generating a development image format so-called bull's-eye format for displaying myocardial image parameters in plural divided regions divided along the myocardial circumferential direction (a direction crossing thickness directions) and a thickness direction, for example. Note that, an arrangement may be made in which a development image format which does not divide the development image in a myocardial thickness direction is generated to display information with respect to the myocardial blood flow perfusion in the myocardial thickness direction.

The myocardial image divided region forming unit 442 has a function of forming divided regions by reading out slice image data of a myocardium from the image database 43 and dividing the slice image data at least in a myocardial thickness direction. As a practical example, myocardial image data is divided radially with centering on a point inside an endocardium, and is further divided in thickness directions of the myocardium, thereby forming divided regions of the myocardial image data.

Figure 7:
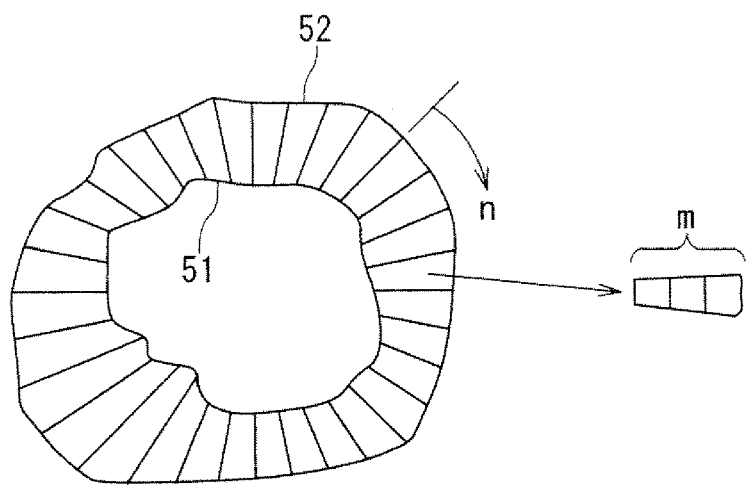
FIG. 7 is a diagram showing an example of divided regions of the myocardial image data formed in the myocardial image divided region forming unit of the computer shown in FIG. 6.

FIG. 7 is a diagram showing an example of divided regions of the myocardial image data formed in the myocardial image divided region forming unit 442 of the computer 32 shown in FIG. 6.

For example, as shown in FIG. 7, the region surrounded by an endocardium 51 and an epicardial contour 52 is divided radially into n regions. FIG. 7 shows an example of radial division, with the number of divisions n=32. Furthermore, each radially divided region is further divided into m regions in diameter directions, i.e., in thickness directions of the myocardium. FIG. 7 shows an example in which the myocardium is divided in the myocardial thickness directions with the number of divisions m=3, thereby dividing the myocardium into three layers, i.e., an inner layer, an intermediate layer, and an outer layer. In a case where each of all the radially-divided regions is divided in the myocardial thickness directions in such a manner, the myocardial image data corresponding to one slice is divided into (n×m) divided regions. Accordingly, in a case where the number of slices is represented by k, the myocardial image data corresponding to the entire left ventricular myocardium is divided into (k×n×m) divided regions. Note that, the myocardial image data can be divided equally in the myocardial thickness directions with setting the number of divisions m, i.e., can be divided equally into m divisions. Alternatively, an arrangement may be made in which each division position in the myocardial thickness directions is set as a ratio to myocardial membrane thicknesses.

Figure 8:
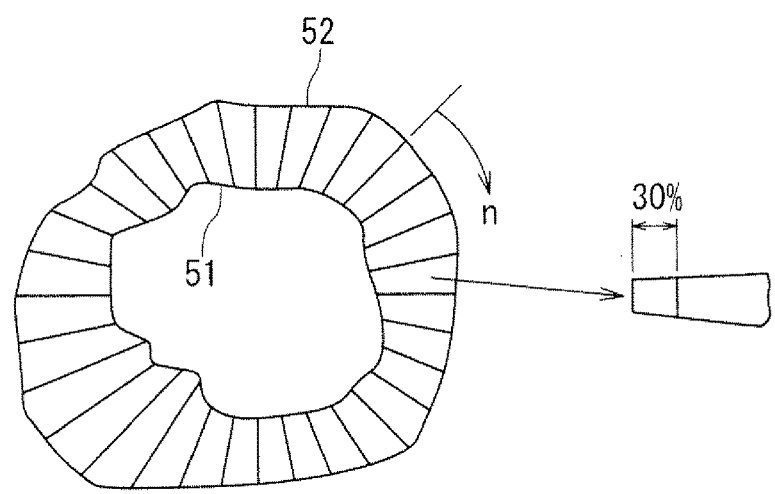
FIG. 8 is a diagram showing another example of divided regions of the myocardial image data formed in the myocardial image divided region forming unit of the computer shown in FIG. 6.

FIG. 8 is a diagram showing another example of divided regions of the myocardial image data formed in the myocardial image divided region forming unit 442 of the computer 32 shown in FIG. 6.

For example, as shown in FIG. 8, an arrangement may be made in which the region surrounded by the endocardium 51 and the epicardial contour 52 is divided radially into n regions, and the division positions in the myocardial thickness directions for each of the radially divided regions are specified as a desired ratio (%) with respect to the myocardial thicknesses. That is to say, in an example shown in FIG. 8, the respective radially-divided regions are divided into two regions with setting the 30%-positions from the side of the endocardium 51 to the myocardial thicknesses as borders.

The parameter calculating unit 443 has a function of calculating desired information based upon pixel values as parameters with respect to each of the myocardial divided regions divided by the myocardial image divided region forming unit 442. Examples of the desired information based upon the pixel values include a parameter obtained based upon a variation of an average pixel value in each divided region over time phase. A graph which represents variation of the average pixel value with regard to time is also referred to as a dynamic curve. Examples of parameters with respect to such dynamic curves include the maximum gradient, the maximum value, the time till the maximum value, the time till the maximum gradient, and a predetermined integrated value. On the other hand, in a case in which image data is acquired by non-dynamic imaging, computation may be performed using values such as the maximum pixel value, the average value, the minimum value, a significant pixel value, etc as parameters based upon the pixel values.

The development image display control unit 444 has: a function of generating development image data for displaying a parameter value corresponding to each of the divided regions in the development image format generated by the development image format generating unit 441 on the display unit 34 with a color scale using desired colors or a gray scale, based upon the desired information based upon the pixel values, e.g., a parameter with respect to a dynamic curve or the like obtained by the parameter calculating unit 443; and a function of displaying a development image of the myocardium on the display unit 34 by providing the generated development image data to the display unit 34.

Figure 9:
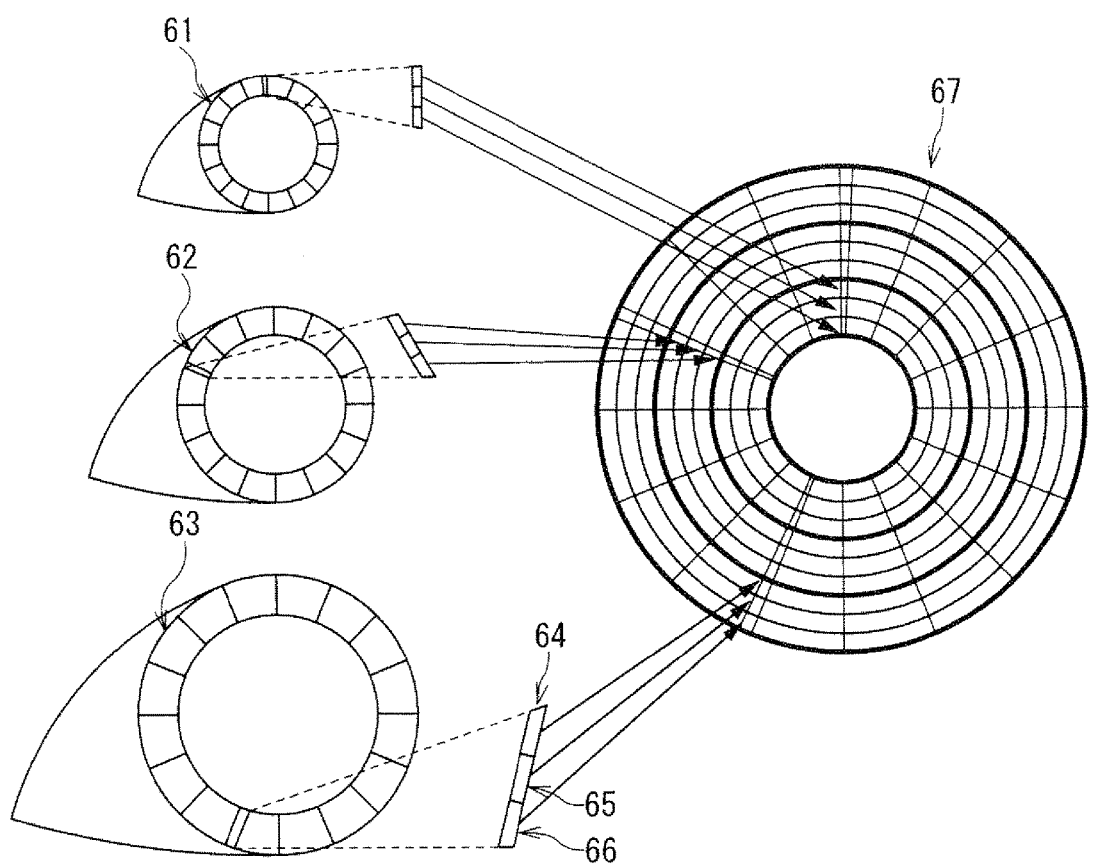
FIG. 9 is a diagram showing the first example of development image data generated in the development image display control unit of the computer shown in FIG. 6.

FIG. 9 is a diagram showing the first example of development image data generated in the development image display control unit 444 of the computer 32 shown in FIG. 6.

As shown in FIG. 9, the myocardial image divided region forming unit 442 divides the myocardial image data corresponding to plural slice positions both in the myocardial thickness directions and in the radial directions, thereby generating plural divided regions for each slice position. In the example shown in FIG. 9, the myocardial image data of each of the apex cordis part 61, the intermediate part 62, and the cardiac base part 63 is divided in the myocardial thickness directions such that it is divided into three regions, i.e., the inner layer 64, the intermediate layer 65, and the outer layer 66. The parameter calculating unit 443 calculates information, such as a parameter or the like, that corresponds to each divided region of the myocardial image data.

Furthermore, the development image format generating unit 441 generates a desired development image format 67. For example, as shown in FIG. 9, the development image format generating unit 441 is capable of generating a development image format 67 which allows all the divided regions obtained by dividing plural slice images in the myocardial thickness directions and the circumferential direction to be displayed as a single development image data. That is to say, like the development image format 67 shown in FIG. 9, the divided regions of the apex cordis part 61 side are arranged on the inner side, and the divided regions of the cardiac base part 63 side are arranged on the outer side. In addition, the divided regions of the inner layer 64 side are arranged on the inner side, and the divided regions of the outer layer 66 side are arranged on the outer side.

Then, the development image display control unit 444 assigns a color or a brightness value, which has been set beforehand based upon the parameter value, to each divided region, thereby generating the development image data.

Figure 10:
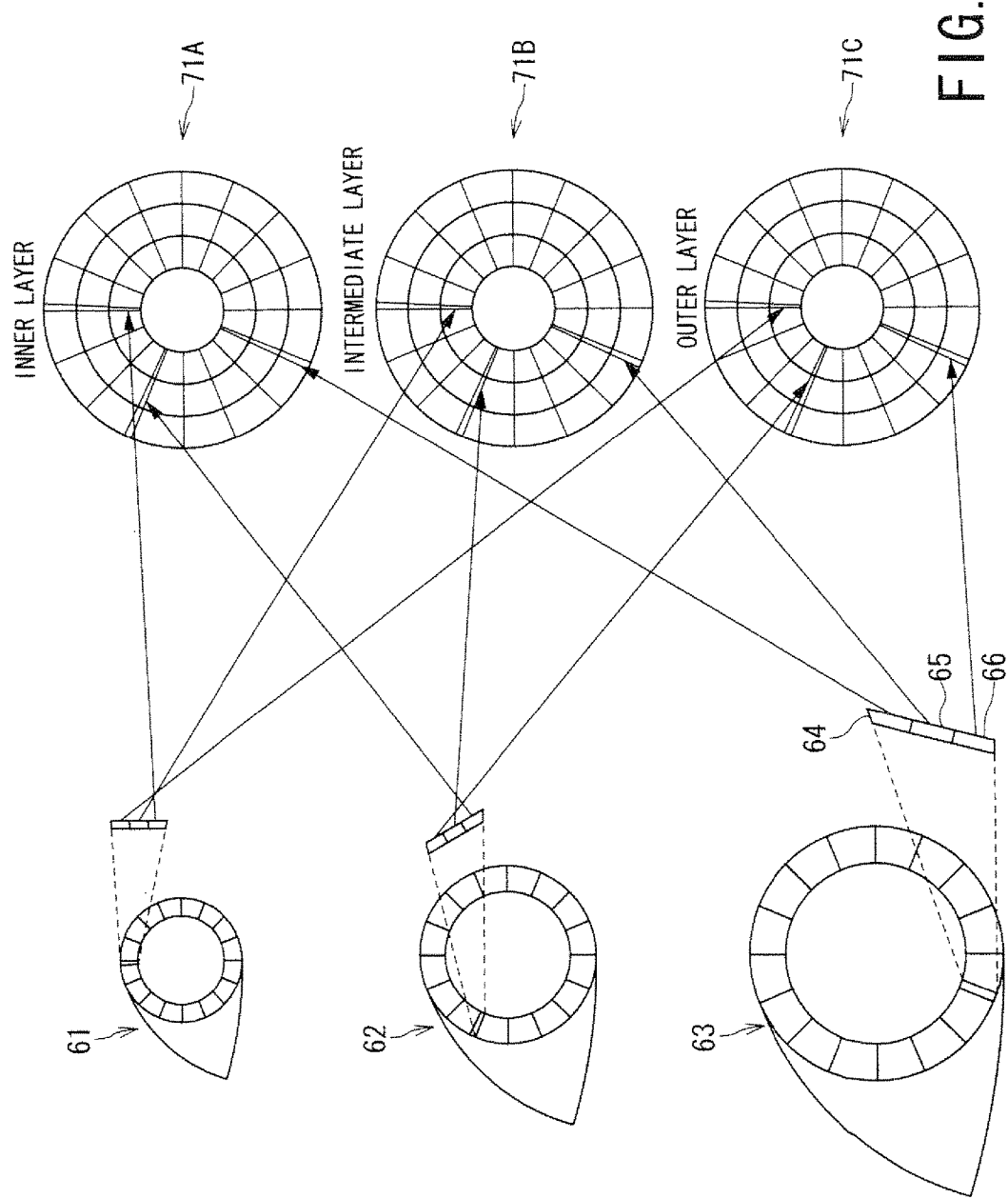
FIG. 10 is a diagram showing the second example of development image data generated in the development image display control unit of the computer shown in FIG. 6.

FIG. 10 is a diagram showing the second example of development image data generated in the development image display control unit 444 of the computer 32 shown in FIG. 6.

The development image format may be formed such that multiple development image data sets 71A, 71B, and 71C are displayed as shown in FIG. 10. In the example shown in FIG. 10, the development image format is created as follows. That is to say, multiple mutually corresponding inner-layer parameters, which have been acquired at different slice positions, are displayed as a common development image data set 71A. Furthermore, multiple mutually corresponding intermediate-layer parameters, which have been acquired at different slice positions, are displayed as a common development image data set 71B. Moreover, multiple mutually corresponding outer-layer parameters, which have been acquired at different slice positions, are displayed as a common development image data set 71C. With such an arrangement, in each of the development image data sets 71A, 71B, and 71C, the divided regions on the apex cordis part 61 side of the myocardium are arranged on the inner side. On the other hand, the divided regions on the cardiac base part 63 side are arranged on the outer side.

Figure 11:
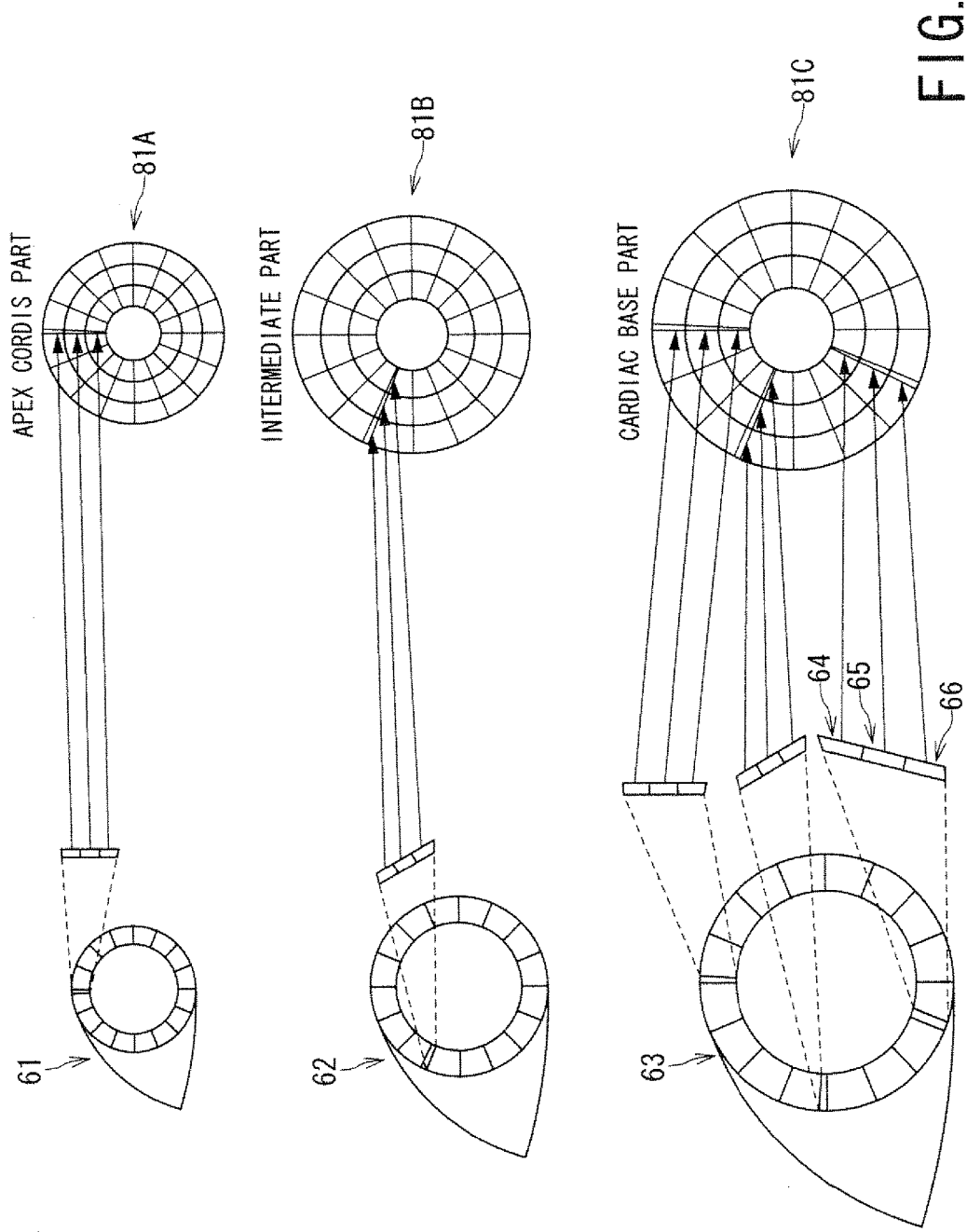
FIG. 11 is a diagram showing the third example of development image data generated in the development image display control unit of the computer shown in FIG. 6.

FIG. 11 is a diagram showing the third example of development image data generated in the development image display control unit 444 of the computer 32 shown in FIG. 6.

As shown in FIG. 11, the development image format may be created such that development image data sets 81A, 81B, and 81C are displayed respectively corresponding to the respective slices. In the example shown in FIG. 11, the development image data sets 81A, 81B, and 81C are created, which correspond to the apex cordis part 61, the intermediate part 62, and the cardiac base part 63, respectively. In each of the development image data sets 81A, 81B, and 81C, the divided regions on the inner layer 64 side are arranged on the inner side, and the divided regions on the outer layer 66 side are arranged on the outer side.

Figure 12:
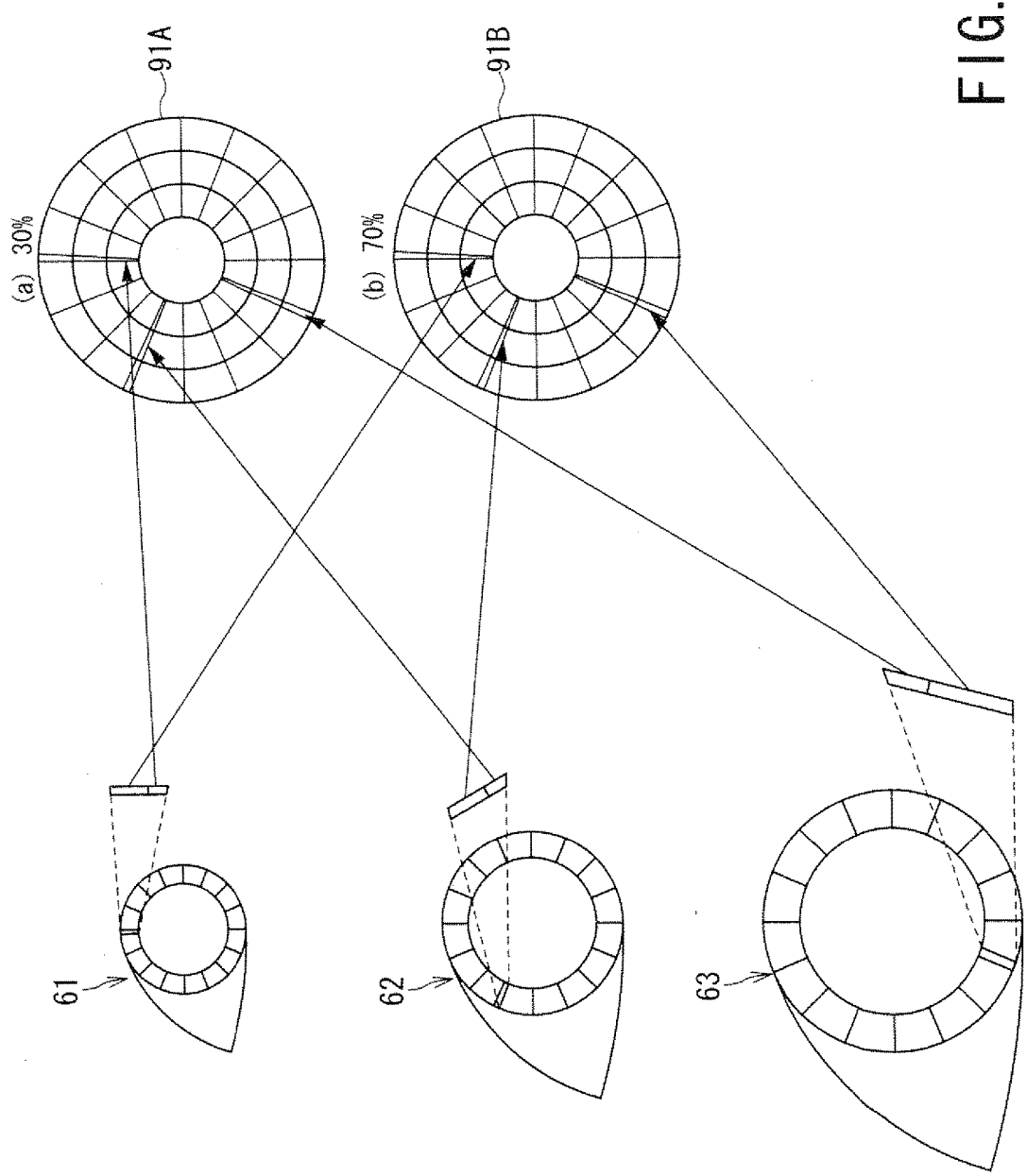
FIG. 12 is a diagram showing the fourth example of development image data generated in the development image display control unit of the computer shown in FIG. 6.

FIG. 12 is a diagram showing the fourth example of development image data generated in the development image display control unit 444 of the computer 32 shown in FIG. 6.

The development image format may be created as shown in FIG. 12. That is to say, a boundary of each divided region with respect to the myocardial thickness directions may be determined as a ratio to thicknesses of the myocardium. Then, each of the development image data set 91A or 91B is displayed for the divided regions mutually corresponding with respect to the myocardial thickness directions. In the example shown in FIG. 12, the first development image data set 91A is created based upon the parameters in the divided regions, of the respective slices, that correspond to 30% parts from the side of the endocardium with respect to the myocardial thicknesses, and the second development image data set 91B is created based upon the parameters in the divided regions, of the respective slices, that correspond to the remaining 70% parts. With such an arrangement, in each of the development image data sets 91A and 91B, the divided regions on the apex cordis part 61 side are arranged on the inner side, and the divided regions on the cardiac base part 63 side are arranged on the outer side.

Note that, an arrangement may be made in which a desired one of the development image data sets 91A and 91B shown in FIG. 12 is displayed, depending upon an imaging purpose. Further, an arrangement may be made which allows an operator to set the ratio to the myocardial thicknesses via a setting screen which displays a user interface such as a scroll bar and a numerical value input box with use of a GUI (Graphical User Interface) technique. With such an arrangement, the development image data sets 91A and 91B may be updated in a real-time manner according to the set ratio to the myocardial thicknesses, and the updated development image data sets 91A and 91B may be displayed on the display unit 34.

As described above, the development image format so that the myocardial image parameters that correspond to different slices may be displayed as parts of a single development image, or may be displayed as parts of separate development images for the respective slices, can be generated. In addition, in a case of dynamic imaging, the slice image data is acquired for plural time phases. Thus, in this case, the development image format may be formed such that a myocardial image parameter that correspond mutually in different time phases is displayed as a single development image or are displayed as separate development images for the respective time phases.

Further, an arrangement may be made in which a single parameter is obtained or selected from among the respective parameters in the regions divided in the myocardial thickness directions, and the development image data is created based upon the obtained or selected parameter, thereby also displaying the development image data as information regarding the myocardial blood flow perfusion in the myocardial thickness directions. Therefore, there is not necessarily a need to divide the development image data in the myocardial thickness directions. Further, an arrangement may be made in which the development image data is created by using a single parameter obtained or selected from the parameters that correspond to plural slices and is displayed as information regarding the myocardial blood flow perfusion in the myocardial thickness directions.

Such display methods provide information with respect to myocardial blood flow perfusion in a myocardial thickness direction. This allows more detailed information to be obtained with respect to the condition of the subendocardial ischemia. Further, a specific divided region may be displayed emphatically, distinctly or selectively according to the parameter values in the divided regions of the development image data so as to allow a portion affected by subendocardial ischemia to be easily identified. For example, an arrangement may be made in which a threshold is set beforehand for a parameter and only an area having a parameter value that exceeds the threshold is selectively displayed. Alternatively, such an area may be highlighted using a different color. With such an arrangement, blood flow perfusion information can be displayed both in the myocardial thickness directions and the circumferential direction at the same time. This allows an operator to visually and easily identify the region or position that corresponds to the subendocardial ischemia in the myocardial thickness directions and the circumferential direction. Note that, the development image display control unit 444 may have a comparison/determination processing function between a parameter and a threshold, a highlight processing function, a selective display processing function, and a discernment display processing function.

Then, the operation and action of the magnetic resonance imaging apparatus 20 will be described.

Figure 13:
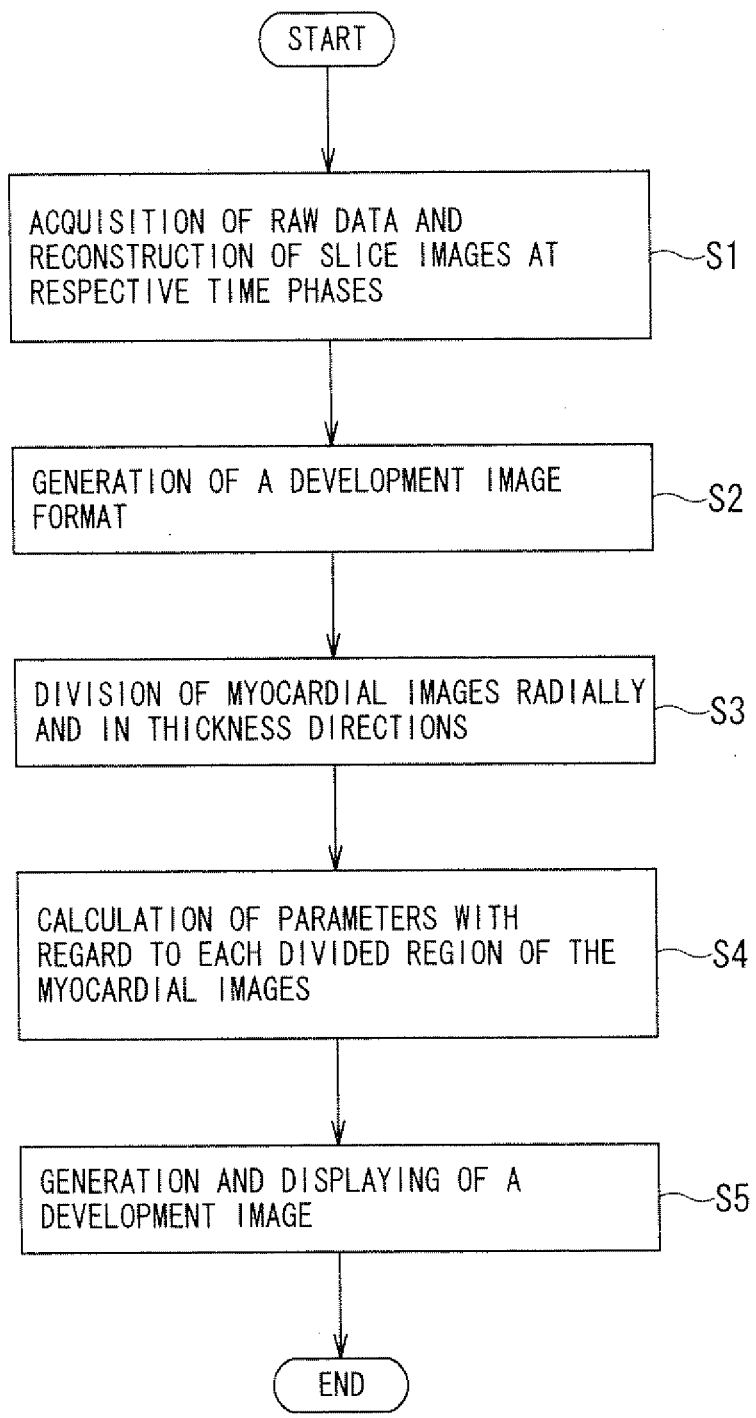
FIG. 13 is a flowchart showing a flow for acquiring cardiac image data and performing display control processing of development image data showing blood flow perfusion information in myocardial thickness directions based on the acquired image data with the magnetic resonance imaging apparatus shown in FIG. 5.

FIG. 13 is a flowchart showing a flow for acquiring cardiac image data and performing display control processing of development image data showing blood flow perfusion information in myocardial thickness directions based on the acquired image data with the magnetic resonance imaging apparatus 20 shown in FIG. 5. Note that, the steps in the flowchart shown in FIG. 13 are not necessarily performed in time series along the described order. That is to say, the flowchart shown in FIG. 13 includes steps which can be performed in parallel or separately.

In step S1, raw data of the heart of the object P is dynamically acquired, and slice image data for each time phase is reconstructed.

For this purpose, the object P is set to the bed 37. Further a static magnetic field is generated at an imaging area of the magnet 21 (a superconducting magnet) for static magnetic field excited in advance by the static-magnetic-field power supply 26. Further, the shim-coil power supply 28 supplies current to the shim coil 22, thereby uniformizing the static magnetic field generated at the imaging area. Subsequently, the input device 33 sends sequence selection information and instruction for starting operation to the sequence controller control unit 40. Then, the sequence controller control unit 40 supplies a sequence acquired from the imaging condition setting unit 45 according to the information inputted by the input device 33 to the sequence controller 31.

The sequence controller 31 drives the gradient power supply 27, the transmitter 29, and the receiver 30 in accordance with the sequence received from the sequence controller control unit 40, thereby generating a gradient magnetic field and in the imaging area where the object P is set, further generating RF signals.

Consequently, the RF coil 24 receives NMR signals generated in the object P, and the received NMR signals are supplied to the receiver 30 sequentially. The receiver 30 receives the NMR signals from the RF coil 24 and generates raw data which is digital data of the NMR signals by signal processing including A/D conversion. The receiver 30 supplies the generated raw data to the sequence controller 31. The sequence controller 31 supplies the raw data to the sequence controller control unit 40. The sequence controller control unit 40 arranges the raw data to the k space generated in the k-space database 41.

As a result, the raw data, corresponding to each slice and time phase, of the heart of the object P is stored in the k-space database 41. Then, the image reconstruction unit 42 performs image reconstruction processing on the raw data stored in the k-space database 41, thereby reconstructing slice image data for each time phase. The reconstructed slice image data is stored in the image database 43.

Subsequently, in step S2, the development image format generating unit 441 generates a desired development image format.

On the other hand, in step S3, the myocardial image divided region forming unit 442 divides the myocardial image data which is the slice image data acquired from the image database 43 both in radial directions around a center point within the endocardium and in the myocardial thickness directions.

Subsequently, in step S4, the parameter calculating unit 443 calculates parameters based upon the pixel values for the respective divided regions of the myocardial image data. For example, an average pixel value is calculated for each of the divided regions. Then, the average pixel values for each of the divided regions are arranged in the time-phase order, thereby obtaining a dynamic curve which represents the change of the average pixel value with respect to the time phase for each divided region. Furthermore, a parameter with respect to the dynamic curve for each divided region is calculated based upon the change of the average pixel value with respect to the time phase for each divided region.

Subsequently, in step S5, the development image display control unit 444 arranges the parameters for the respective divided regions in the divided regions formed by the development image format formation unit 441 respectively, thereby generating the development image data. The development image display control unit 444 displays the development image data thus generated on the display unit 34.

Such an arrangement allows the operator to observe a development image of the myocardium displayed on the display unit 34 visually, thereby allowing the operator to easily obtain information with respect to myocardial blood flow perfusion in the myocardial thickness direction.

That is, the above-described magnetic resonance imaging apparatus 20 is an apparatus configured to generate development image data according to a development format that allows information with respect to blood flow perfusion in a myocardial thickness direction to be displayed based upon slice image data of a heart. Thus, such an arrangement allows information with respect to blood flow perfusion in a myocardial thickness direction to be easily obtained, which is impossible by conventional techniques. Thus, such an arrangement allows details of range and/or position of a portion that is affected by subendocardial ischemia to be recognized easily at an early stage.

Note that, the present invention is not restricted to such an arrangement including the magnetic resonance imaging apparatus 20. Rather, any medical image diagnostic apparatus having a high spatial resolution such as an X-ray CT (computed tomography) apparatus may include a built-in image processing apparatus that corresponds to the display control unit 44 shown in FIG. 6. Thus, such an arrangement also allows information with respect to blood flow perfusion in a myocardial thickness direction to be obtained and displayed based upon slice image data of a heart. Alternatively, an image processing apparatus having the above-described functions may be connected via a network with a medical image diagnostic apparatus, an image server, or another image processing apparatus.

Description has been made above regarding an arrangement in which cross section images are acquired with respect to the left ventricular short axis of a heart. Further, an arrangement may be made in which data is acquired with respect to another cross section, and subsequently multi-planar reconstruction is performed so as to produce a left ventricular short axis cross sectional image of the heart.

Further, in the above-described example, though processing and displaying with regard to myocardial perfusion images are performed, the development image format and the development image data according to such a development image format described above can be generate in case of developing and displaying another image used in a cardiac examination, e.g., a contrast-enhanced myocardial delay image.

In many cases, slice image data of heart is contrast-enhanced slice image data acquired with injection of a contrast medium into the object P. However, slice image data of heart may be non-contrast-enhanced slice image data acquired without injection of a contrast medium into the object P.

For example, the magnetic resonance imaging apparatus 20 can selectively acquire NMR signals from blood flow without contrast medium with applying an ASL (arterial spin labeling) pulse to tag the blood flow, and generate non-contrast-enhanced slice image data of the heart based upon the acquired NMR signals. More specifically, non-contrast-enhanced blood flow image data of heart can be produced by obtaining a difference between image data generated based on NMR signals acquired with applying an ASL pulse and image data generated based on NMR signals acquired without applying an ASL pulse. Imaging with applying an ASL pulse may be performed as non-dynamic imaging. Accordingly, the slice image data may be data corresponding to a specific time phase. Even in this case, an arrangement may be made which calculates parameters based upon pixel values in the divided regions obtained by dividing a single slice image data set corresponding to the specific time phase in the myocardial thickness directions, and the development image data is generated by using the obtained parameter, thereby allowing blood flow perfusion information in a myocardial thickness direction to be displayed.

What is claimed is:

1. An image processing apparatus comprising:
an image data acquisition unit configured to acquire slice image data for different cross-sectional wall portions of a heart of an object;
a development generating unit configured
　(a) to obtain blood flow perfusion data with respect to plural points within each of plural myocardial wall regions that are divided both radially across a myocardial thickness direction and circumferentially along the myocardial wall cross-section within each said cross-sectional wall portion based on the slice image data, and
　(b) based on the blood flow perfusion data, to generate development display data according to a predetermined bulls-eye development format wherein each cross-sectional myocardial wall region is divided both radially across a myocardial wall thickness direction and circumferentially along the myocardial wall cross-section within each cross-sectional wall portion to present at least two predetermined concentric circumferentially extending sets of radially-divided myocardial wall regions, and wherein the whole interior of each divided wall region is displayed with its own assigned visually perceptible display form based on the obtained blood flow perfusion data for said plural points therewithin such that all points within a divided wall region have the same visually perceived value; and
a display unit configured to display the development display data.

2. The image processing apparatus of claim 1, wherein:
said development generating unit is configured to generate plural sets of development display data with regard to plural cardiac time phases based on plural sets of slice image data corresponding to the plural cardiac time phases.

3. The image processing apparatus of claim 1, wherein:
said development generating unit is configured to generate plural sets of development display data representing mutually different slice positions based on plural sets of slice image data corresponding to the different slice positions.

4. The image processing apparatus of claim 1, wherein:
said development generating unit is configured to generate development display data according to a development format that represents wall thickness divided concentrically and radially from a cardiac base part of the heart toward an apex cordis part.

5. The image processing apparatus of claim 1, wherein:
said image data acquisition unit is configured to obtain contrast enhanced slice image data acquired by injecting a contrast medium into the object.

6. The image processing apparatus of claim 1, wherein:
said image data acquisition unit is configured to obtain non-contrast enhanced slice image data acquired without injecting a contrast medium into the object.

7. The image processing apparatus of claim 6, wherein:
said image data acquisition unit is configured to acquire magnetic resonance image data as the non-contrast enhanced slice image data by applying an arterial spin labeling pulse.

8. An image processing apparatus comprising:
an image data acquisition unit configured to acquire slice image data for different cross-sectional wall portions of a heart of an object;
a development generating unit configured
　(a) to calculate first development display data with respect to each of plural myocardial wall regions that are divided both radially across a myocardial wall thickness direction and circumferentially along the myocardial wall cross-section within each said cross-sectional wall portion based on at least one pixel value in each divided wall region, and
　(b) based on the first development display data, to generate second development display data according to a predetermined bulls-eye development format wherein each cross-sectional myocardial wall region is divided both radially across a myocardial wall thickness direction and circumferentially along the myocardial wall cross-section within each cross-sectional wall portion to present at least two predetermined concentric circumferentially extending sets of radially-divided myocardial wall regions, and wherein all points within a divided wall region are displayed with the same assigned visually perceptible display form based on said at least one pixel value in that divided wall region; and
a display unit configured to display the second development display data.

9. The image processing apparatus of claim 8, wherein:
said development generating unit is configured to generate plural sets of said first and second development display data representing plural cardiac time phases based on plural sets of slice image data corresponding to the plural cardiac time phases.

10. The image processing apparatus of claim 8, wherein:
said development generating unit is configured to generate plural sets of said first and second development display data representing mutually different slice positions based on plural sets of slice image data corresponding to the different slice positions.

11. The image processing apparatus of claim 8, wherein:
said development generating unit is configured to generate said first and second development display data according to a development format that represents wall thickness divided concentrically and radially from a cardiac base part of the heart toward an apex cordis part.

12. The image processing apparatus of claim 8, wherein:
said image data acquisition unit is configured to obtain contrast enhanced slice image data acquired by injecting a contrast medium into the object.

13. The image processing apparatus of claim 8, wherein:
said image data acquisition unit is configured to obtain non-contrast enhanced slice image data acquired without injecting a contrast medium into the object.

14. The image processing apparatus of claim 8, wherein:
said development generating unit is configured to calculate a parameter, with respect to each of the divided wall regions, obtained based on variation of an average pixel value in each of the divided wall regions as a function of elapsed time phase as the first and second development display data based on pixel value.

15. The image processing apparatus of claim 8, wherein: said development generating unit is configured to calculate the first and second development display data with respect to each of the divided wall regions based on pixel values in each of the divided wall regions with respect to each of plural slice images of the slice image data and to generate a single set of said first and second development display data according to a predetermined bulls-eye development format by which a divided wall region in an inner layer side of a myocardium represents an inside divided wall region and a divided wall region in an outer layer side of the myocardium represents an outside divided wall region.

16. The image processing apparatus of claim 8, wherein: said development generating unit is configured to calculate the first and second development display data with respect to each of the divided wall regions based on pixel values in each of the divided wall regions with respect to each of plural slice images of the slice image data and to generate the first and second development data with respect to each of the slice images according to a predetermined bulls-eye development format by which a divided wall region in an inner layer side of a myocardium is represented by an inside divided wall region of the bulls-eye second development display data and a divided wall region in an outer layer side of the myocardium is represented by an outside divided wall region of the bulls-eye second development display data.

17. The image processing apparatus of claim 8, wherein: said development generating unit is configured to calculate the first and second development display data with respect to each of the divided wall regions based on pixel values in each of the divided wall regions with respect to each of plural slice images of the slice image data and to generate sets of the first and second development data respectively representing the divided wall regions in a common slice image of the slice image data, each of the sets including its divided wall regions correlated to those of other different slice images according to a predetermined bulls-eye development format by which an apex cordis wall section of a myocardium is represented by an inside divided wall region and a cardiac base wall section of the myocardium is represented by an outside divided wall region.

18. The image processing apparatus of claim 8, wherein: said development generating unit is configured to calculate the first and second development display data based on pixel values in each divided wall region divided at a line corresponding to a predetermined percentage of wall thickness of a myocardium.

19. The image processing apparatus of claim 8, wherein: said development generating unit is configured to generate the first and second development data of which a specific divided wall region is displayed emphatically, distinctly or selectively according to a value of the development display data based on pixel value.

20. An image diagnostic apparatus comprising:
an image data acquisition unit configured to acquire slice image data for different cross-sectional wall portions of a heart of an object by imaging of the heart;
a development generating unit configured
 (a) to obtain blood flow perfusion data with respect to each of plural points within each of plural divided wall regions divided both radially across a myocardial thickness direction and circumferentially along the myocardial wall cross-section within each said cross-sectional wall portion based on the slice image data, and
 (b) to generate, based on the blood flow perfusion data, development display data according to a predetermined bulls-eye development format wherein each cross-sectional myocardial wall region is divided both radially across a myocardial wall thickness direction and circumferentially along the myocardial wall cross-section within each cross-sectional wall portion to present at least two predetermined concentric circumferentially extending sets of radially-divided myocardial wall regions, and wherein the whole interior of each divided wall region is displayed with its own assigned visually perceptible display form based on the blood flow perfusion data therewithin such that all points within a divided wall region have the same visually perceived value; and
a display unit configured to display the second development display data.

21. The image diagnostic apparatus of claim 20, wherein: said image acquisition unit is configured to acquire magnetic resonance image data as the slice image data.

22. An image processing method comprising:
acquiring slice image data for different cross-sectional wall portions of a heart of an object;
obtaining blood flow perfusion data with respect to each of plural divided myocardial wall regions that are divided both radially across a myocardial wall thickness direction and circumferentially along the myocardial wall cross-section within each said cross-sectional wall portion based on the slice image data; and
generating, based on the blood flow perfusion data, development display data according to a predetermined bulls-eye development format wherein each cross-sectional myocardial wall region is divided both radially across a myocardial wall thickness direction and circumferentially along the myocardial wall cross-section within each cross-sectional wall portion to present at least two predetermined concentric circumferentially extending sets of radially-divided myocardial wall regions, and wherein the whole interior of each divided wall region is displayed with its own assigned visually perceptible display form based on the obtained blood flow perfusion data therewithin such that all points within a divided wall region have the same visually perceived value; and
displaying the development display data.

23. An image processing method comprising:
acquiring slice image data for different cross-sectional wall portions of a heart of an object;
calculating first development display data with respect to each of plural divided myocardial wall regions that are divided both radially across a myocardial thickness direction and circumferentially along the myocardial wall cross-section within each said cross-sectional wall portion based on pixel values in each divided wall region;
generating, based on the first development display data, second development display data according to a predetermined bulls-eye development format, wherein each cross-sectional myocardial wall region is divided both radially across a myocardial wall thickness direction and circumferentially along the myocardial wall cross-section within each cross-sectional wall portion to present at least two predetermined concentric circumferentially extending sets of radially-divided myocardial wall regions, and wherein the whole interior of each divided wall region is displayed with its own assigned visually perceptible display form based on the obtained pixel values therewithin such that all points within a divided wall region have the same visually perceived value; and displaying the second development display data.

* * * * *